United States Patent [19]

Jackson

[11] 4,444,205
[45] Apr. 24, 1984

[54] APPARATUS FOR ASSESSING JOINT MOBILITY

[75] Inventor: John Jackson, Strathclyde, Scotland

[73] Assignee: University of Strathclyde, Glasgow, Scotland

[21] Appl. No.: 267,471

[22] Filed: May 27, 1981

[30] Foreign Application Priority Data

May 31, 1980 [GB] United Kingdom ............... 8017898

[51] Int. Cl.³ .............................................. A61B 5/10
[52] U.S. Cl. ................................. 128/782; 128/774; 338/114
[58] Field of Search ............... 128/782, 781, 779, 774, 128/639, 644, 721; 73/379, 381, 769, 787, 855; 33/174 D; 338/2, 5, 47, 114

[56] References Cited

U.S. PATENT DOCUMENTS

| | | | |
|---|---|---|---|
| 2,734,978 | 2/1956 | Bulgin | 338/114 |
| 3,124,769 | 3/1964 | Peterson | 338/2 |
| 3,268,845 | 8/1966 | Whitmore | 128/721 X |
| 3,565,080 | 2/1971 | Ide et al. | 128/782 X |
| 3,572,322 | 3/1971 | Wade | 128/640 |
| 3,719,913 | 3/1973 | DuBose et al. | 338/2 |
| 3,815,611 | 6/1974 | Denniston | 128/782 X |
| 3,820,529 | 6/1974 | Gause et al. | 128/782 |
| 3,836,900 | 9/1974 | Mansfield | 128/721 |
| 3,863,625 | 2/1975 | Viglione et al. | 128/732 |
| 3,937,212 | 2/1976 | Fletcher et al. | 128/782 |
| 3,991,745 | 11/1976 | Yoslow et al. | 33/174 D X |
| 4,019,377 | 4/1977 | Rickards | 73/855 X |
| 4,152,748 | 5/1979 | Arkans | 128/779 X |
| 4,195,643 | 4/1980 | Pratt, Jr. | 128/779 |
| 4,231,225 | 11/1980 | Haski et al. | 128/774 X |
| 4,258,100 | 3/1981 | Fujitani et al. | 338/114 X |
| 4,258,720 | 3/1981 | Flowers | 128/721 X |
| 4,306,571 | 12/1981 | McLeod, Jr. | 128/782 |

FOREIGN PATENT DOCUMENTS

| | | |
|---|---|---|
| 2187109 | 1/1974 | France . |
| 1107826 | 3/1968 | United Kingdom . |
| 178029 | 1/1966 | U.S.S.R. ............... 128/782 |

OTHER PUBLICATIONS

Johnson et al., "Goniometer for Continuous Recording of Knee Angle", Med. and Biol. Eng. and Comput., 3-1981, pp. 255-256, vol. 19, No. 2.

Johnson et al., "A Mechanical Transducer for Phallography", Biomed. Eng. 9-1968, pp. 416-418.

Ramirez et al., "Pattern Recognition of Mult. Tests Values as a Diagnostic Tool", Comput. Biol. Med., vol. 2, 1972, pp. 39-44.

Barker et al., "Distributed Microprocessor System for the Detection and Diagnosis of Cardiac Arrhythmias", Dept. of E.E., Univ. of Aston in Birmingham Proceedings of Conf. on Microproc. in Autom. & Comm., No. 41, 9-1978, pp. 83-92.

Primary Examiner—Lee S. Cohen
Assistant Examiner—Angela D. Sykes
Attorney, Agent, or Firm—Gerald Ferguson, Jr.; Joseph J. Baker

[57] ABSTRACT

Apparatus is provided which enable the assessment of mobility of human and/or animal joints to be carried out. A flexible transducer includes a conductive elastomer which, when stretched, provides a change in an electrical output signal. The transducer is located over the joint to be investigated and during movement of the joint electrical signals from the transducer output which are a function of joint mobility, are produced. The signals are digitized and stored in a memory and are compared with a bank of data from normal and pathological subjects stored in a continuously updated memory. When the comparison locates the 'best fit' between the joint movement and the stored data, the type of joint movement is classified and the result is presented on a visual display unit. The movement signal can be conditioned so that the angular displacement of the joint, the rate of joint movement, acceleration of the joint can be estimated and classified. The force produced by the joint can also be calculated using the acceleration and an estimate of the mass moved. This system permits the progress of an individual to be monitored and to identify joint movement characteristics in particular patient populations.

The transducer, when combined in a composite unit with electrodes is also used to accurately assess the degree of neuromuscular activity during and after anaethesia.

5 Claims, 10 Drawing Figures

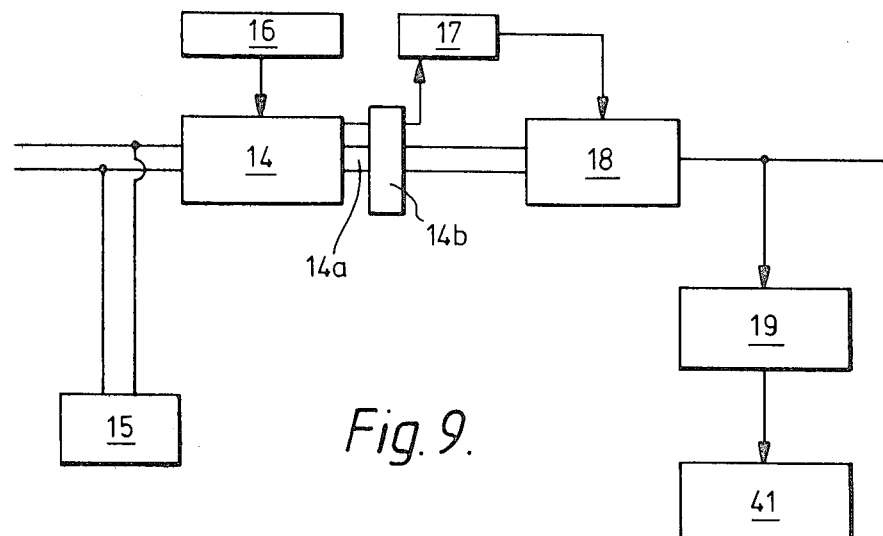
Fig. 9.
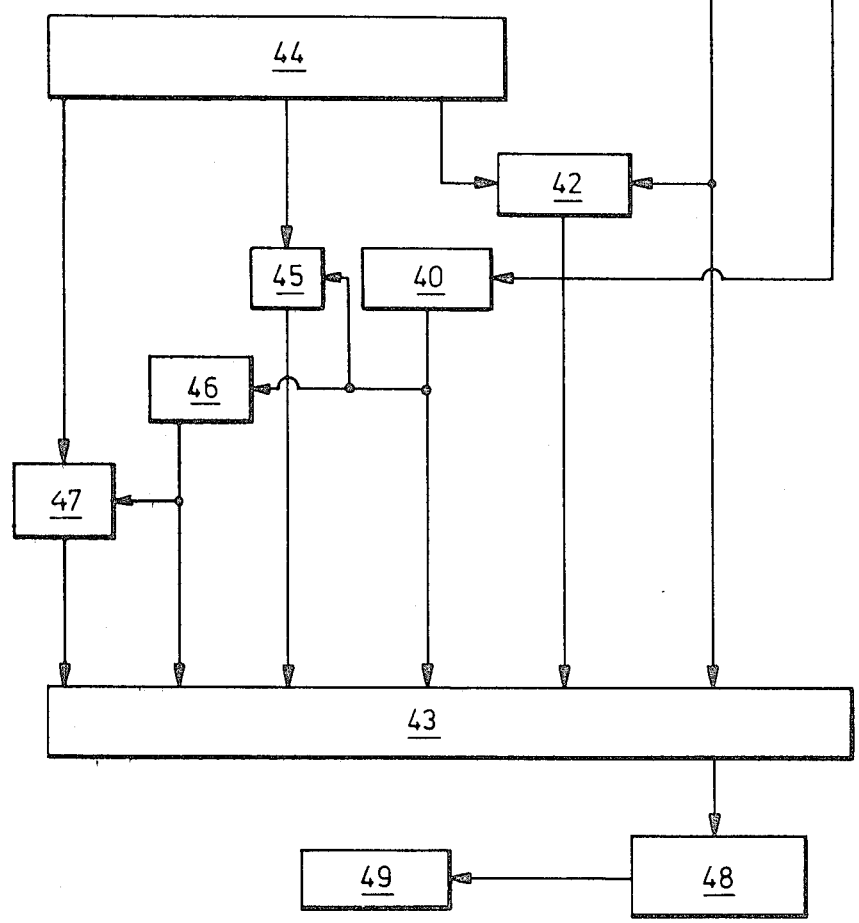

APPARATUS FOR ASSESSING JOINT MOBILITY

METHOD AND APPARATUS FOR ASSESSING JOINT MOBILITY

The present invention relates to apparatus and a method for measuring particularly, but not exclusively, the mobility of human and/or animal joints. Moreover, the apparatus comprises two principal features; devices for obtaining a signal from a joint, the signal being representative of joint mobility, and means for processing this signal into a result which is useful for indicating the condition of the joint.

As is known in the art, devices for obtaining a signal which is representative of mobility from a joint exist, such as goniometers. Such devices have to be located directly over or on the joint to work effectively, which can result in erroneous measurements due to the movement of the joint being restricted or unnaturally modified. This is considered a disadvantage of these devices. Such devices may also be large with respect to joint sizes and also require to be used with expensive instrumentation. In this latter case they are impractical to move to locations where diagnosis of joint symptoms is required for example, local clinics.

These devices also require considerable expertise to fit over the joint, and the limb carrying the joint is often clamped to prevent movement. This is time-consuming and may further modify the movement of the joint.

Another known type of device used for measuring joint mobility is a piezoelectric or load cell force plate, this has been primarily used for investigating lower limb joints. However, these signals obtained are units of force, therefore to obtain a value of joint movement sophisticated instrumentation is required to calculate acceleration and thus integrated to give displacement. This usually requires a television camera monitoring system connected to a computer such as a PDP11 or PDP12, which is expensive and unsuitable for field use. Furthermore, the data from several points are accumulated in one signal, and the signal has to be analysed to assess the mobility contribution of each joint. Data can be lost in this procedure and hence the accuracy of results obtained is limited.

An object of the present invention is to obviate or mitigate the abovesaid disadvantages.

According to a first aspect of the present invention there is provided a transducer for obtaining a signal indicative of mobility from human and/or animal joint comprising a conducting elastomeric member adapted to be located over a joint, means for locating the elastomeric member over the joint, the transducer being connectable to an electrical supply and having an electrical output which varies with the length of the conducting elastomer whereby in use, when the joint moves, the elastomer changes length and the electrical output from the transducer is varied.

Embodiments of the present invention will now be described by way of example with reference to the accompanying drawings in which:

FIG. 9 is a block diagram of the signal processing circuitry according to the present invention for use with the transducers shown in FIGS. 1 and 5.

Figure 1:
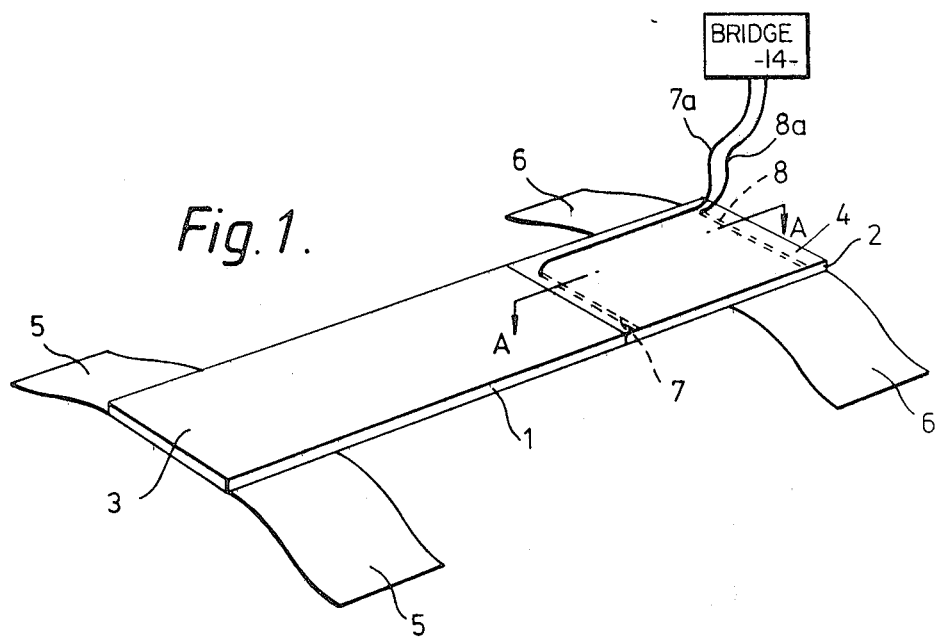
FIG. 1 is a schematic diagram of a joint mobility transducer according to the invention.

Referring now to FIG. 1, a flexible elastic member 1 is secured to a conductive elastomer 2. The elastic member 1 and the elastomer 2 have respective generally planar shaped surfaces 3, 4 providing a strip form adapted to be securely mounted over a joint by straps 5 and 6 respectively. Alternatively, the straps 5 and 6 may be secured by adhesive. Two electrodes 7 and 8 are inserted within the elastomer 2. The electrodes 7 and 8 are connected by leads 7a and 8a respectively to an electrical resistance bridge network 14 such that the conductive elastomer 2 forms one arm of the bridge 14.

Figure 2:
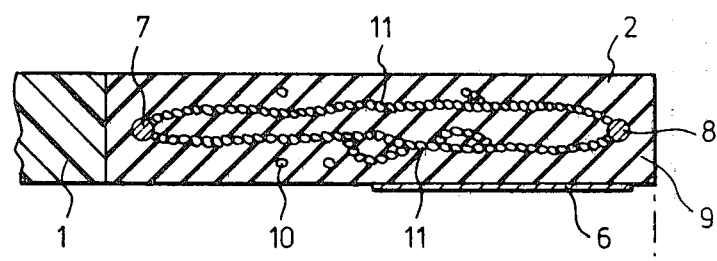
FIG. 2 is a view of part of FIG. 1 taken along A—A.
Figure 3:
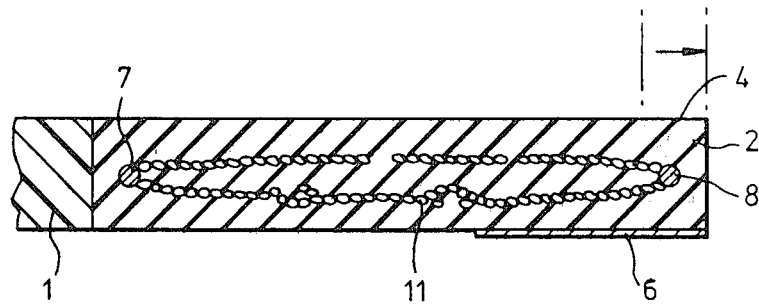
FIG. 3 is similar to FIG. 2 and shows the elastomer when extended.

The elastomer 2 is composed of a non-conductive silicone-based rubber 9 with particles of carbon 10 homogeneously dispersed therein (FIG. 2). A number of conductive paths, of which only two conductive paths 11 are shown in the interest of clarity, are formed by contact between adjacent carbon particles 10 and electrodes 7 and 8. When the elastomer is extended by movement of the joint, the number of conductive pathways decrease (FIG. 3) thus altering the conductivity of the material between the electrodes 7 and 8, and hence the resistance.

Figure 4:
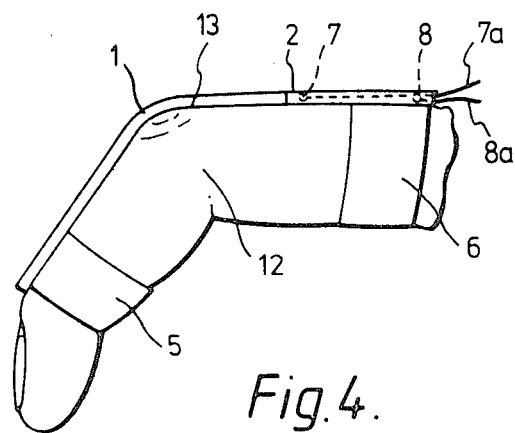
FIG. 4 is a schematic diagram of the apparatus of FIG. 1 located over a flexed human finger joint.

In use the device is located over a proximal interphalangeal (PIP) finger joint 12 for example and fastened to the finger by the straps 5 and 6 as shown in FIG. 4, such that the flexible elastic member 1 tranverses the joint contour 13 with the conductive elastomer being located proximal to the joint 12. When the electrical apparatus is connected, the resistance bridge is balanced for no joint movement.

When the joint is flexed the flexible member 1 transmits a tensile force (not shown) to the elastomer 2, which then stretches in accordance with its modulus of elasticity. The change in geometry of the member 2 alters the number of conductive paths between the electrodes 7 and 8 (FIG. 3) resulting in a change in the resistance of the elastic member 2. Thus the resistance bridge 14 is unbalanced and the electrical output from the bridge 14 is directly related to tensile force measured, which in turn is dependent on the mobility of the joint.

Figure 5:
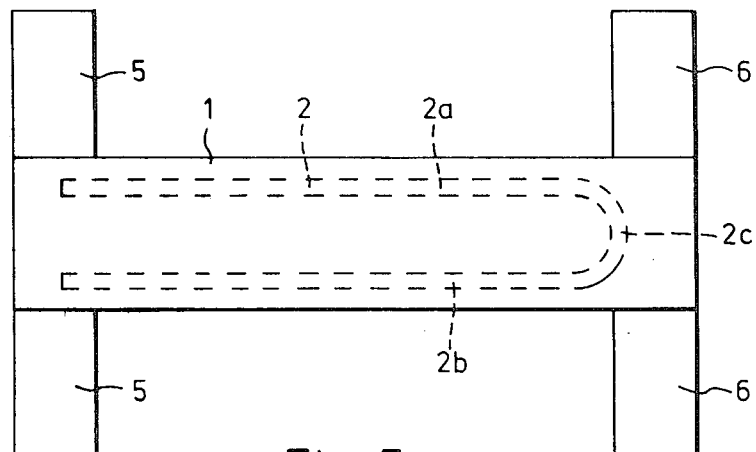
FIG. 5 is a schematic diagram of an alternative type of joint mobility transducer, according to the invention.

Referring now to FIG. 5, a second embodiment according to the present invention is shown. The conducting elastomer 2 is formed into a U-shape and has two leg portions 2a, 2b joined by a neck portion 2c. The portions 2a, 2b are parallel and are co-planar. Straps 5, 6 are located at each end of the transducer 1 as shown in FIG. 5. The arrangement of the elastomer in the non-conducting silicon rubber 9 is the same as before. Alternatively, a single strip of elastomer may be located along the length of the transducer 1.

In use, the strip per se is flexible enough to be located over a joint and, as the joint moves tensile force is transmitted to the elastomer which extends and thus the electrical resistance of the bridge 14 is varied.

Figure 6:
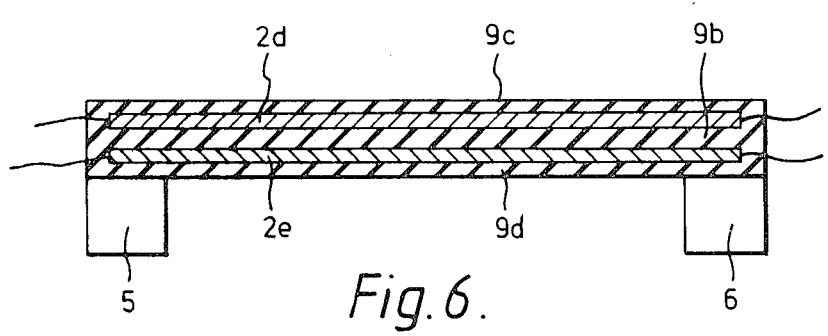
FIG. 6 is a schematic diagram of another alternative joint mobility transducer according to the invention.

Referring now to FIG. 6, a third embodiment according to the present invention is shown. The transducer 1 has two identical strips 2d, 2e of conducting elastomer located one on top of the other in parallel. The strips are separated by a layer of non-conducting elastomer 9b, and each upper and lower surface of the strips 2d, 2e is covered by respective layers of non-conducting elastomer 9c, 9d. Straps 5, 6 are positioned at each end of the transducer 1. Each conducting elastomer 2d, 2e has two leads attached thereto. The respective input leads and output leads of each conducting elastomer may be connected together.

In use, the transducer 1 is located by the straps 5, 6 over a joint. When the joint moves the strips 2d, 2e are stretched by different amounts due to the curvature over the joint, thus the resistance change due to the stretching is different for each elastomer, that is, a differential resistance change is produced. The signal corresponding to the differential resistance change unbalances the bridge 14, and thus the tensile force and the mobility of the joint can be assessed.

In addition, in each of the embodiments, a further elastomer strip of a length identical to the elastomer members being stretched may be incorporated into the transducer; this further elastomer strip is not stretched and acts as a reference for strain determinations. The non-strained elastomer strip could be used as an arm of the bridge to eliminate common-mode variables such as temperature and humidity. In a further alternative arrangement, at least one non-strained elastomer strip could be provided for each strained strip to provide better elimination of the common-mode variables.

Any number of similar transducers of the described embodiments could be used for example, two could be placed in parallel, one on either side of the spine, to measure lateral movement of the vertebrae. Also transducers of the type described in the third embodiment could be used to provide information of anterior/posterior flexion and extension of the spine and also lateral movement.

The transducer as described in the aforementioned embodiments may be of particular benefit when used as a monitor for assessing the degree of neuromuscular activity during and after anaesthesia in patients who are recovering from the effects of neuromuscular blocking drugs. Neuromuscular blocking drugs act in such a way to reduce the effect of nerve stimulation of skeletal muscle. It is important to be able to determine quickly and accurately the level of anaesthesia immediately following operations for a variety of reasons; the principal reason being the patients well-being.

One way of determining the degree of neuromuscular activity during and after anaesthesia which has been proposed involved electrical stimulation of the ulnar nerve on the volar surface of the forearm. Estimations of the degree of neuromuscular block are made using the movement of the thumb under the action of the adductor pollicis muscle, by a transducer attached to the thumb by a thread.

A disadvantage of this type of apparatus is that the stimulation of the ulnar nerve produces inconsistent movements of the thumb; the system is not sensitive enough to discriminate between small changes in the degree of neuromuscular activity, and the system does not provide a result conveniently proportional to the degree of neuromuscular activity.

It is an object of the present invention to obviate or mitigate against these disadvantages.

In accordance with a further aspect of the invention, the foregoing transducer is used to monitor movement of a joint induced by electrical stimulation means to monitor the degree of neuromuscular activity before and after anaesthesia, as will now be described.

Figure 7:
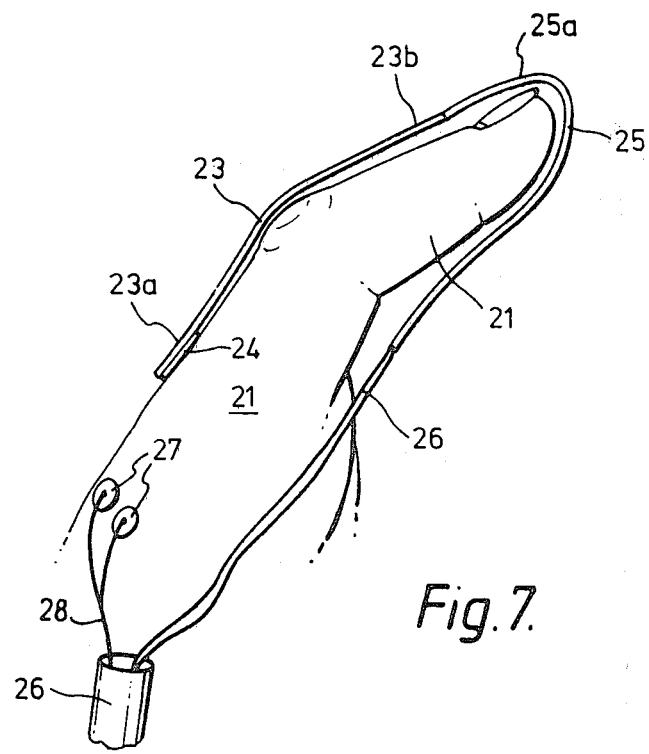
FIG. 7 is a schematic diagram showing apparatus according to the present invention located over a thumb.

Referring now to FIG. 7 of the drawings, apparatus for monitoring the degree of neuromuscular activity of the drug is shown located on a thumb 21. The apparatus comprises a transducer 23 secured at one end 23a to the skin by an adhesive pad 24 and at the other end 23b to one end 25a of a thumb end cover 25. The thumb end cover is shaped to cover the tip of the thumb and may be flexible or rigid. The other end of the cover 25 is attached to a connecting strip 26 which contains the leads (not shown) connecting the transducer to the signal processing circuitry. A pair of electrodes 27 are placed over the median nerve proximal to the transducer, the electrode leads 28 being also carried in the connecting strip 26. The electrodes may be retained in place by adhesive pads (not shown).

In use electrical pulses are applied from a stimulator (not shown in the interest of clarity) to the electrodes 27, the pulses are applied in standard patterns i.e. a train of four pulses or single pulses followed by tetanic stimulation. When the median nerve is stimulated the opponens pollicis muscle contracts and the thumb moves towards the lateral aspect of the hand, extending the transducer.

The signals from the transducer are sent to a signal processing unit 30 (FIG. 8) and are decoded therein to provide an indication of the degree of neuromuscular activity.

The signal processing unit includes a stimulator 31 from which electrical pulses are sent to the electrodes 27. The signals from the transducer 23 are analogue and are converted to digital signals in an A/D converter 32. The stimulator 31 and the A/D convertor 32 are both connected to a microprocessor 33. The microprocessor 33 is also connected to a read-only-memory (ROM) and/or a random access memory (RAM) unit 34, and may be connected to a printer 35 and to an external control unit such as central 'host' computer via an input/output (I/O) unit 36. The stimulator 31 may be adjusted by a manual control 31a connected thereto.

The ROM/RAM unit 34 contains programs for, stimulation patterns to be applied to the nerve, for the input/output control routines and the processing of information provided by the transducer.

In use, during or after the operation, and knowing the type of drug used, a stimulation pattern of pulses to be applied to the electrode is selected by a selector 37; each pulse applied to the nerve resulting in a movement of the thumb which in turn produces a change in the resistance of the transducer. The stimulation forms may be a train of four pulses (or the) given at 0.5 second intervals, the train being repeated every 10 seconds. Frequency pulse is 1 HZ or 0.1 Hz.

Figure 8:
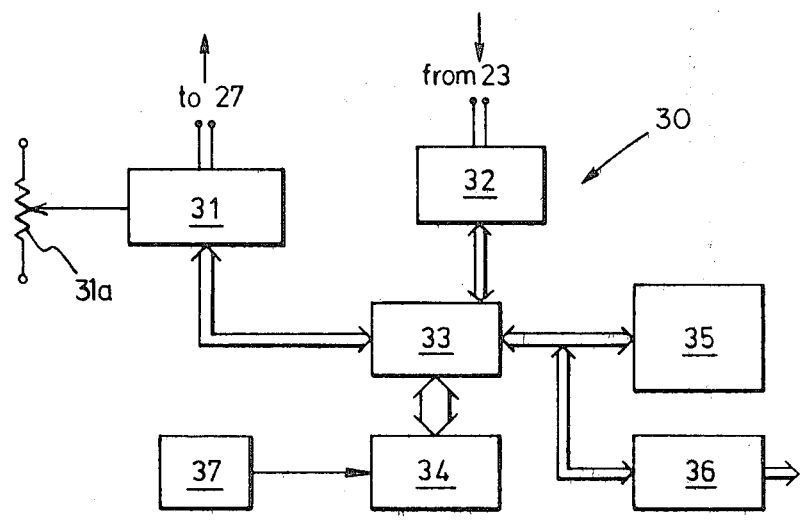
FIG. 8 is a block diagram of the circuitry used to operate the apparatus shown in FIG. 7.

The magnitude of the pulses produced by the stimulator is of a constant current type having a failsafe cut-off and is variable either by the microprocessor or manually. A constant current level is continuously passed through the transducer and when the resistance changes, a voltage change across the transducer proportional to the change in length of the transducer is produced. The signal processing circuit measures the base-line level between pulses, and the height of each pulse and calculates and records the difference between the two levels. As aforementioned this result may be achieved using a bridge network. The successive difference values can be displayed graphically as bars or in some other form, the difference value levels being proportional to the magnitude of thumb movement. Alternatively in the circuit as shown in FIG. 8, the data can be digitally analysed and the output graphically displayed on a printer or VDU. With the digital system it is relatively straight-forward to provide a temporal comparison between successive pulse heights; this data could also be stored and displayed providing a clear indication of the effectiveness of the drug.

In accordance with safety regulations associated with anaesthetic drugs, the apparatus is constructed explosion-proof.

The signal processing circuit incorporates features which mitigate the risk of electrical hazard to patients; the current applied to the electrodes is isolated from the electrical power supply of the signal processing unit by a transformer. In addition, the level of the current and voltage applied to the electrodes and to the transducer is monitored to ensure that proper electrical contact is made.

Without departing from the scope of the invention it should be understood that several modifications may be made to the apparatus. For example, several signal processing units may be used to interface with a central processing unit to monitor data from several patients. The transmission of data from the transducer to the monitor may be achieved by telemetry, and the apparatus could also be battery powered. The use of the ROM and/or RAM unit 34 permits the programs stored therein to be altered to give flexibility in selecting a particular stimulation pattern e.g. for use with a new drug or with certain patients.

Advantages of the second aspect of the present invention include; the transducer is attached to the joint under investigation, it is not limited to use with median nerve/opponens pollicis neuromuscular system, the stimulation electrodes and the transducer can be combined in a one piece unit, the use of complementary-metal-oxide semiconductor (CMOS) circuitry including erasable programmable read-only-memories (EPROM's) which require very low power to operate facilitate the use of a battery powered system which is portable and offers increased electrical safety.

The signal processing circuitry according to a third aspect the present invention normalises data obtained from joint movements in the time domain and in the signal amplitude domain; thus all joint movement signals can be presented in a standard form and date from one patient can be compared with normal date or date representative of certain pathological conditions. In addition, if a patient is undergoing therapy for a condition that involves movement of a joint, the treatment can be monitored at successive stages giving an indication of progress.

The circuitry will be best explained if only one transducer is considered connected thereto.

Referring now to FIGS. 1, 5 and FIG. 9, the conductive elastomer 2 is connected to a bridge 14 and to a failsafe circuit 15. The failsafe circuit 15 prevents a voltage or current surge from entering the transducer and also checks that the transducer is properly connected.

The bridge 14 is balanced so that the bridge output 14a is set to zero when there is no movement and hence strain applied to the transducer 2. The bridge 14 is also connected to a calibration and checking circuit 16 which is switchable into the signal processing circuit, and, when switched in, provides constant value signals corresponding to transducer signals which check the operation of the signal processing circuit. The output of the bridge 14a is connected to an analogue to digital (A/D) converter 14b. The output of the A/D converter 14b is connected to a random access memory (RAM) 17 and to a noise eliminator 18. The output of the RAM 17 is also connected to the noise eliminator 18. The output of the noise eliminator 18 is connected to an amplitude normalising circuit 19 and to a rate calculator 40. The output of the amplitude normalising circuit 19 is connected to a time-base normalising circuit 41 the output of which is connected to a comparator 42 and to a visual display unit 43.

The comparator 42 is also connected to a read only memory (ROM) 44 and has its output connected to the visual display unit (VDU) 43. The output of the rate calculator 40 is connected to a first data fitting program store (D.f.pl) 45 and to the VDU 43 and to a differentiating means 46. The Dfp 45 is connected to the ROM 44 and has its output connected to the VDU 43. The output of the differentiating means 46 is connected to a second data fitting program store (Dfp2) 47 and to the VDU 43. The other input of the Dfp2 47 is connected to the ROM 44 and its output is connected to the VDU 43.

The output of the VDU 43 is connected to a second random access memory (RAM) 48 which contains a record of basic and processed data permitting comparison between successive transducer signals. The RAM 48 is connected to a recorder 49 for providing a 'hard' copy of the results. In use, when the transducer is located over a joint as shown in FIG. 4, for example, and the joint is moved the transducer gives an output, the bridge 14 is unbalanced and the bridge output signal 14a is digitised and stored in the RAM 17 to be processed at a later time. The output signal is also integrated by the noise eliminator 18 to remove noise. A series of readings are taken as the joint is moved through a prescribed routine.

The integrator output signal is amplitude normalised on a standard 100% scale. The output signal from the amplitude normalising circuit 19 is normalised in the time domain in the time-base normalising circuit 41 which condenses zero movement to full movement on a 100% time scale. It is also possible to use the initial movement to set the zero range limit.

The output signal from the time-base normalising circuit 41 is compared with a store of normal and pathological data for certain conditions by a curve fitting program in the comparator 42.

In order to ascertain whether the movement of the joint correlates with any known pathology, the angle magnitude, rate and the acceleration of joint movement can be calculated, by differentiating the basic magnitude signal in the rate calculator 40 and differentiating means 46 respectively. The signals corresponding to angle, magnitude, rate and acceleration of joint movement are in the forms of 'curves' and can be compared with appropriate curves from data fitting programmes Dfp 42, Dfp 45 and Dfp 47 respectively. The force exerted by the joint can also be calculated from the acceleration of the joint.

The magnitude, rate and acceleration curves can be displayed on the VDU 43, as can each signal from the data fitting program comparators Dfp 42, Dfp 45 and Dfp 47.

Figure 10:
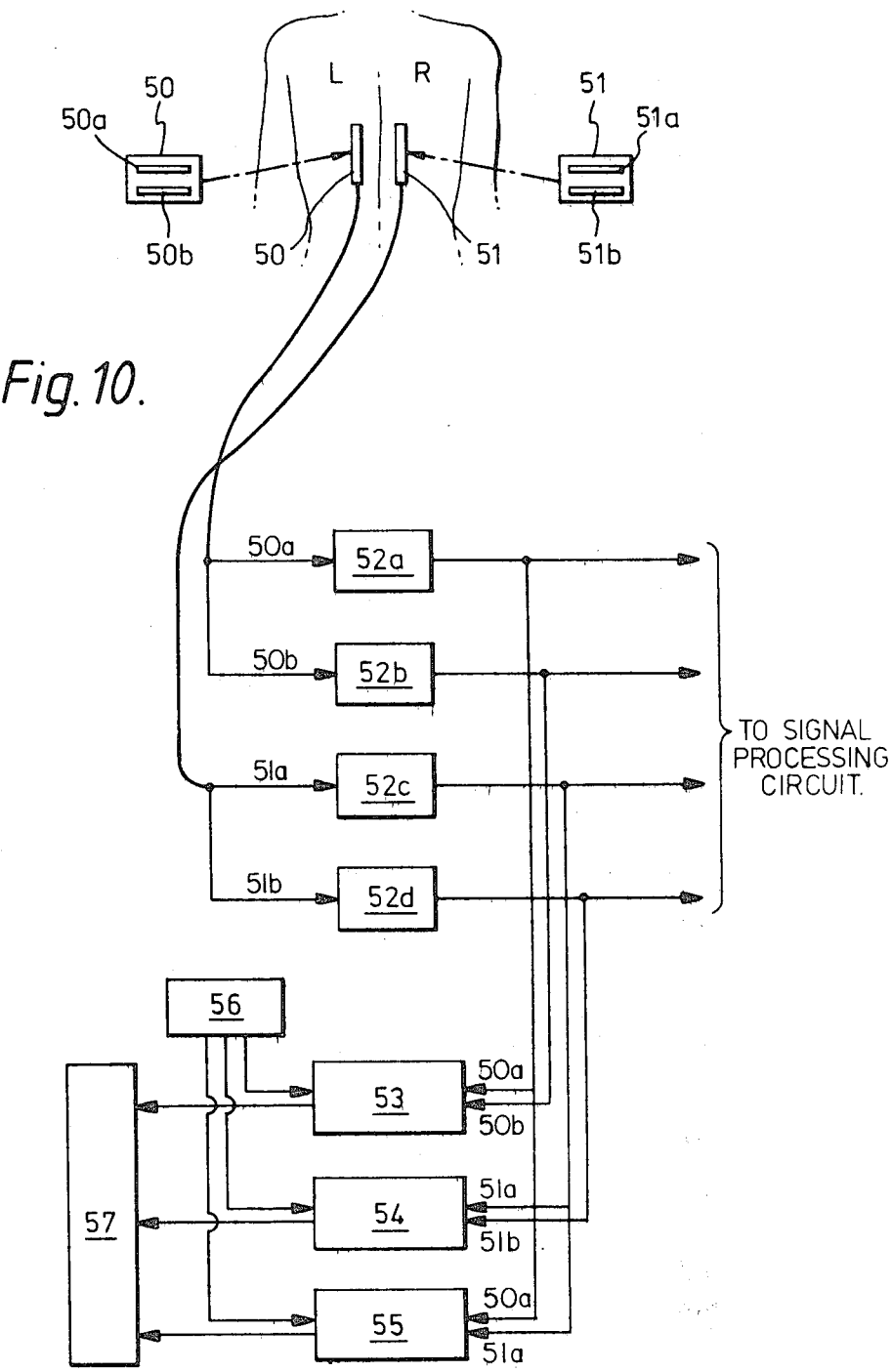
FIG. 10 is a block diagram of the signal processing circuitry according to the present invention for use with the transducer shown in FIG. 6.

Referring now to FIGS. 6 and 10, the lateral, and the anterior/posterior movement of the spine may be obtained by positioning laminated transducers 50, 51 on each side of the spinal ridge. Lateral movement of the spine is then assessed by comparing the output of one laminated transducer with the other. In each transducer 50, 51 there are two separate transducers 50a, 50b and 51a, 51b respectively. The output signals of the transducers are fed to respective noise elinimators 52a, to 52d which eliminate background noise. The output of each noise eliminator is fed to the signal processing circuit. Pairs of output signals from the noise eliminators 52a, to 52d are fed to comparators 53, 54 and 55; outputs 52a and 52b being fed to comparator 53; outputs 52c and 52d being fed to comparator 54, and outputs 52a and 52c are fed to comparator 55.

The said comparators are connected to a calibrated RAM 56 which is used to calibrate the transducers with a mechanical calibration unit before the transducers are applied to the patient. This contains data of the resistance change for a certain angular displacement for a particular transducer or transducers.

Comparator 53 gives a value of the flexion/extension angle of the left side of the spine. Comparator 54 gives a value of the flexion/extension angle for the right side of the spine. Comparator 55 gives a value of the lateral movement of the spine i.e. left lateral or right lateral depending on the relative magnitude of the input signals.

The outputs of comparators 53, 54 and 55 are displayed on VDU 57. The aforementioned circuitry according to the third aspect of the invention may be achieved by logic circuits or by firmware.

With regard to the firmware, software controlled microprocessor—based circuitry processes the analogue transducer signals into digital signals and then normalises the time and signal amplitude ranges to the same 100% ranges as data of normal and pathological conditions which are stored in a programmable memory means. The result of the comparison which is indicative of a particular joint mobility is obtained and presented to a tester, in visual or audio form. For example, the result could be graphically displayed on a VDU or on a printer of any other suitable display means.

The stored joint movement signal and the stored data in the memory can be processed by differentiating the signals to provide an indication of the mobility classification of the rate of joint movement and the acceleration of joint movement. The other parameters such as angular displacement and the force exerted by the joint may be assessed in a similar manner.

The information which is stored in the memories relating to normal and to pathological conditions may be continuously updated in accordance with aquisition of new data.

Without departing from the scope of the invention combinations of circuit components of FIGS. 9 and 10 have application for:

use by physicians and surgeons in the diagnosis of human joint conditions or for use by veterinary surgeons for animal condition diagnosis e.g. race horses; use by physiotherapists and by sports/football trainers so that the effectiveness of treatment can be assessed in the clinic using circuit components 14, 15, 17, 18, 19, 41, 43 and 48; monitoring the post-operative recovery of anaesthetised patients using circuit components 2, 3, 4, 5, 8, 16. Movements of the thumb are recorded so that recovery from neuromuscular blocking drugs can be assessed; use in isolated muscle preparations using circuit components 23, 14, 15, 17, 18 and 49 and measuring the articulation of moving mechanical parts within a machine or the stresses on fixed structure using circuit components 1, 23 or 30, 14, 15, 17, 18 and 49. The method of fixing the transducer would be altered accordingly.

Thus there is provided a signal processing circuit which accurately records joint mobility information and which provides results classifying the mobility of the joint independent of positioning over the joint by an operator.

What I claim is:

1. Apparatus for obtaining a signal indicative of mobility of a skeletal joint, comprising an assembly formed by a pair of like members physically oriented in parallel and mutually separated by a non-electrically-conductive elastomer, each said member being made of a material which is both elastomeric and electrically conductive having an electrical resistance which varies with elastic extension and contraction of the member, positioning means on the assembly for positioning both members of the assembly simultaneously at a joint to be tested such that movement of the joint elastically extends and contracts both members of the assembly whereby the electrical resistance of each member is varied, a resistance-sensitive electrical network, conductor means connected to each said member and interconnecting each said member with said electrical network to provide a pair of electrical outputs from said network which vary, in use, with movement of the joint under test.

2. Apparatus as claimed in claim 1, wherein said material is composed of a homogeneous mixture of nonconductive elastomer and conductive particles dispersed therein, a plurality of conductive pathways between said conductor means being formed in each said member by mutual contact of adjacent conductive particles, the number of conductive pathways being varied with elastic extension and contraction of each member.

3. Apparatus as claimed in claim 1, wherein each said member is U-shaped having a pair of parallel limbs one end of each limb being free and the other end of each limb being mutually interconnected, each limb having a longitudinal extent said positioning means are adapted for positioning the assembly at a joint to be tested such that movement of the joint elastically extends and contracts the longitudinal extent of each limb of said U-shape, and said conductor means are connected to each member at the free ends of the limbs of said U-shape.

4. Apparatus for determining the mobility classification of a skeletal joint, comprising a member made of a material which is both elastomeric and electrically conductive having an electrical resistance which varies with elastic extension and contraction of the member,
positioning means on the member for positioning the member at a joint to be tested such that movement of the joint elastically extends and contracts the elastic member whereby the electrical resistance of the member is varied,
a resistance-sensitive electrical network,
conductor means connected to said member and interconnecting said member with said electrical network to provide an electrical output from said network which varies, in use, with movement of the joint under test, an analogue-to-digital converter connected to said electrical network for digitising the electrical output thereof, identifying means connected to the output of the converter for identifying from the digital data thereby provided at least one characteristic of the joint under test, memory means pre-programmed with digital information representing at least said one characteristic of a plurality of known skeletal joints, comparator means connected to said memory means and to said identifying means and arranged to compare at least said one characteristic of the joint under test with that of the known skeletal joints, and output means connected to the comparison means for presenting a comparator result of identity as indicative of the mobility classification in respect of said one characteristic of the joint under test.

5. Apparatus as claimed in claim 4, wherein the digital information with which said memory means is pre-programmed is relative to predetermined amplitude and time scales, and said identifying means includes normalising means from which said at least one characteristic of the joint under test is identified on said predetermined amplitude and time scales.

* * * * *